US00PP17427P2

(12) United States Plant Patent
Bhandary

(10) Patent No.: US PP17,427 P2
(45) Date of Patent: Feb. 20, 2007

(54) ***AGLAONEMA* PLANT NAMED 'INDO-PRINCESS'**

(50) Latin Name: *Aglaonema hybrida*
Varietal Denomination: Indo-Princess

(75) Inventor: Kudoor Raghunath Bhandary, Bangalore (IN)

(73) Assignee: Sunshine Foliage World, Zolfo Springs, FL (US)

( * ) Notice: Subject to any disclaimer, the term of this patent is extended or adjusted under 35 U.S.C. 154(b) by 0 days.

(21) Appl. No.: 11/188,974

(22) Filed: Jul. 25, 2005

(51) Int. Cl.
*A01H 5/00* (2006.01)

(52) U.S. Cl. ..... Plt./376

(58) Field of Classification Search ..... Plt./376
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Aglaonema* plant named 'Indo-Princess', characterized by its upright and outwardly arching plant form; relatively rapid growth rate; freely clumping habit and short internodes; full, dense and bushy appearance; broadly lanceolate leaves with acuminate apices; leaves positioned roughly horizontally to outwardly arching; upper leaf surfaces with grey green-colored leaves with darker grey green and dark green-colored spots forming chevrons and dark green-colored margins; green-colored leaf petioles with sparse and random pale yellow-colored spots and streaks; and tolerance to low temperatures.

2 Drawing Sheets

Botanical denomination: *Aglaonema hybrida.*
Cultivar designation: 'Indo-Princess'.

BACKGROUND OF THE INVENTION

The present Invention relates to a new and distinct cultivar of *Aglaonema* plant, botanically known as *Aglaonema hybrida* and hereinafter referred to by the name 'Indo-Princess'.

The new *Aglaonema* is the result of a planned breeding program conducted by the Inventor in Bangalore, India. The objective of the breeding program is to create new compact *Aglaonema* cultivars with compact and dense plant habit and unique and attractive leaf coloration.

The new *Aglaonema* originated from a cross-pollination made by the Inventor in 1990 of the *Aglaonema commutatum* cultivar Malay Lady, not patented, as the female, or seed, parent with the *Aglaonema hybrida* cultivar Abidjan, not patented, as the male, or pollen, parent. The new *Aglaonema* was discovered and selected by the Inventor in 1991 as a single plant within the progeny of the stated cross-pollination in a controlled environment in Bangalore, India. The new *Aglaonema* was selected on the basis of its compact plant habit and attractive foliage coloration.

Asexual propagation of the new cultivar by vegetative cuttings since June, 2000 in a controlled environment in Zolfo Springs, Fla., has shown that the unique features of this new *Aglaonema* are stable and reproduced true to type in successive generations.

SUMMARY OF THE INVENTION

The following traits have been repeatedly observed and are determined to be the unique characteristics of 'Indo-Princess'. These characteristics in combination distinguish 'Indo-Princess' as a new and distinct cultivar of *Aglaonema:*

1. Upright and outwardly arching plant form.
2. Relatively rapid growth rate.

3. Freely clumping habit and short internodes; full, dense and bushy appearance.
4. Broadly lanceolate leaves with acuminate apices.
5. Leaves positioned roughly horizontally to outwardly arching.
6. Attractive leaf coloration; upper leaf surfaces with grey green-colored leaves with darker grey green and dark green-colored spots forming chevrons and dark green-colored margins.
7. Green-colored leaf petioles with sparse and random pale yellow-colored spots and streaks.
8. Tolerant to low temperatures.

In side-by-side comparisons conducted by the Inventor in Bangalore, India, plants of the new *Aglaonema* differed from plants of the female parent, the *Aglaonema commutatum* cultivar Malay Lady, in the following characteristics:

1. Plants of the new *Aglaonema* were taller than plants of the cultivar Malay Lady.
2. Plants of the new *Aglaonema* were more freely clumping than plants of the cultivar Malay Lady.
3. Plants of the new *Aglaonema* had broader leaves than plants of the cultivar Malay Lady.
4. Plants of the new *Aglaonema* and the cultivar Malay Lady differed in leaf coloration as plants of the cultivar Malay Lady had dark green-colored leaves with irregular grey green-colored bands.

In side-by-side comparisons conducted by the Inventor in Bangalore, India, plants of the new *Aglaonema* differed from plants of the male parent, the *Aglaonema hybrida* cultivar Abidjan, in the following characteristics:

1. Plants of the new *Aglaonema* were more compact than plants of the cultivar Abidjan.
2. Plants of the new *Aglaonema* were more freely clumping than plants of the cultivar Abidjan.
3. Plants of the new *Aglaonema* had smaller leaves than plants of the cultivar Abidjan.

4. Plants of the new *Aglaonema* and the cultivar Abidjan differed in leaf coloration as plants of the cultivar Abidjan had silver gray-colored leaves with irregular green-colored veinal bands and faint gray green-colored patches.

Plants of the new *Aglaonema* can also be compared to plants of the cultivar Silver Queen, not patented. In side-by-side comparisons conducted in Bangalore, India, plants of the new *Aglaonema* differed from plants of the *Aglaonema* cultivar Silver Queen in the following characteristics:

1. Plants of the new *Aglaonema* grew more rapidly than plants of the cultivar Silver Queen.
2. Plants of the new *Aglaonema* had larger leaves than plants of the cultivar Silver Queen.
3. Plants of the new *Aglaonema* and the cultivar Silver Queen differed in leaf coloration as plants of the cultivar Silver Queen were lighter green in color.
4. Plants of the new *Aglaonema* were more low temperature tolerant than plants of the cultivar Silver Queen.

Plants of the new *Aglaonema* can also be compared to plants of the cultivar Maria Christina, not patented. In side-by-side comparisons conducted in Bangalore, India, plants of the new *Aglaonema* differed from plants of the *Aglaonema* cultivar Maria Christina in the following characteristics:

1. Plants of the new *Aglaonema* grew more rapidly than plants of the cultivar Maria Christina.
2. Plants of the new *Aglaonema* were more freely clumping than plants of the cultivar Maria Christina.
3. Plants of the new *Aglaonema* had larger leaves than plants of the cultivar Maria Christina.
4. Plants of the new *Aglaonema* and the cultivar Maria Christina differed in leaf coloration as plants of the cultivar Maria Christina were lighter green in color.
5. Plants of the new *Aglaonema* were more low temperature tolerant than plants of the cultivar Maria Christina.

BRIEF DESCRIPTION OF THE PHOTOGRAPHS

The accompanying colored photographs illustrate the overall appearance of the new *Aglaonema,* showing the colors as true as it is reasonably possible to obtain in colored reproductions of this type. Colors in the photographs may differ slightly from the color values cited in the detailed botanical description which accurately describe the colors of the new *Aglaonema.*

The photograph on the first sheet comprises a side perspective view of a typical plant of 'Indo-Princess'.

The photograph on the second sheet is a close-up view of typical leaves of 'Indo-Princess'.

DETAILED BOTANICAL DESCRIPTION

Plants of the cultivar Indo-Princess have not been observed under all possible environmental conditions. The phenotype may vary somewhat with variations in environment such as temperature and light intensity without, however, any variance in genotype.

The aforementioned photographs and following observations and measurements describe plants of the new *Aglaonema* that were grown in 25-cm containers, in Zolfo Springs, Fla., in a polypropylene-covered shadehouse with light levels about 2,000 to 3,000 foot-candles. During the production of the plants, day temperatures ranged from 23° C. to 35° C. and night temperatures ranged from 16° C. to 26° C. Plants used for the photographs and description were about one year from planting. Color references are made to The Royal Horticultural Society Colour Chart, 1995 Edition, except where general terms of ordinary dictionary significance are used.

Botanical classification: *Aglaonema hybrida* cultivar Indo-Princess.

Parentage:

*Female, or seed, parent.*—*Aglaonema commutatum* cultivar Malay Lady, not patented.

*Male, or pollen, parent.*—*Aglaonema hybrida* cultivar Abidjan, not patented.

Propagation:

*Type.*—By vegetative cuttings.

*Time to initiate roots.*—Summer: About 12 to 15 days at 27° C. Winter: About 20 to 24 days at 16° C.

*Time to produce a rooted plant.*—Summer: About one month at 27° C. Winter: About two months at 16° C.

*Root description.*—Thick, fibrous, fleshy, and freely-branching.

Plant description:

*Plant form.*—Erect when young, becoming outwardly arching as leaves develop; inverted triangle, symmetrical and uniform.

*Vigor/growth rate.*—Vigorous; relatively rapid growth rate. Plant size appropriate for 25-cm containers.

*Growth habit.*—Freely clumping habit; plants typically produce about 16 offshoots per plant; full, dense and bushy appearance.

*Plant height.*—About 46 cm.

*Plant width* (*spread*).—About 72 cm.

*Stem description.*—Length: About 15 cm. Diameter: About 1.4 cm. Internode length: About 1.2 cm. Aspect: Upright to outwardly arching. Strength: Good. Color: 147A.

*Foliage description.*—Appearance: Single; clasping. Length: About 26.2 cm. Width: About 10.2 cm. Shape: Broadly lanceolate. Apex: Acuminate. Base: Obtuse to cordate. Margin: Entire; undulating. Orientation: Initially upright to roughly horizontal to outwardly arching. Texture: Mostly smooth, slightly rugose; glabrous; thick and leathery. Veins: Slightly recessed on upper surface and prominent on lower surface. Venation pattern: Pinnate. Color: Developing and fully expanded leaves, upper surface: Close to 191A to 191B; spots forming chevrons, 189A to more green than 189A and some darker green than 147A; margins, darker green than 147A. Developing and fully expanded leaves, lower surface: Closest to 137A. Venation, upper surface: Midvein, close to 147A; lateral veins, similar to lamina. Venation, lower surface: Midvein, close to 146A; lateral veins, similar to lamina. Petiole: Aspect: Erect to bent. Length: About 12.2 cm. Diameter, distal: About 1.5 cm. Diameter, proximal: About 4 mm. Wing length: About 8.4 cm. Wing diameter: About 7.5 mm. Color, petiole and wing: Close to 147A with sparse and random spots and streaks, close to 4D.

Inflorescence description: Inflorescence development has not been observed on plants of the new *Aglaonema* grown under shadehouse production conditions.

Disease/pest resistance: Plants of the new *Aglaonema* have been observed to be resistant to root pathogens common to *Aglaonema* such as *Phytophthora.* Plants of the new

*Aglaonema* have not been observed to be resistant to pests and other pathogens common to *Aglaonema*.

Weather tolerance: Plants of the new *Aglaonema* have been observed to be tolerant to wind, rain and temperatures ranging from 7 to 41° C.

It is claimed:

1. A new and distinct cultivar of *Aglaonema* plant named 'Indo-Princess', as illustrated and described.

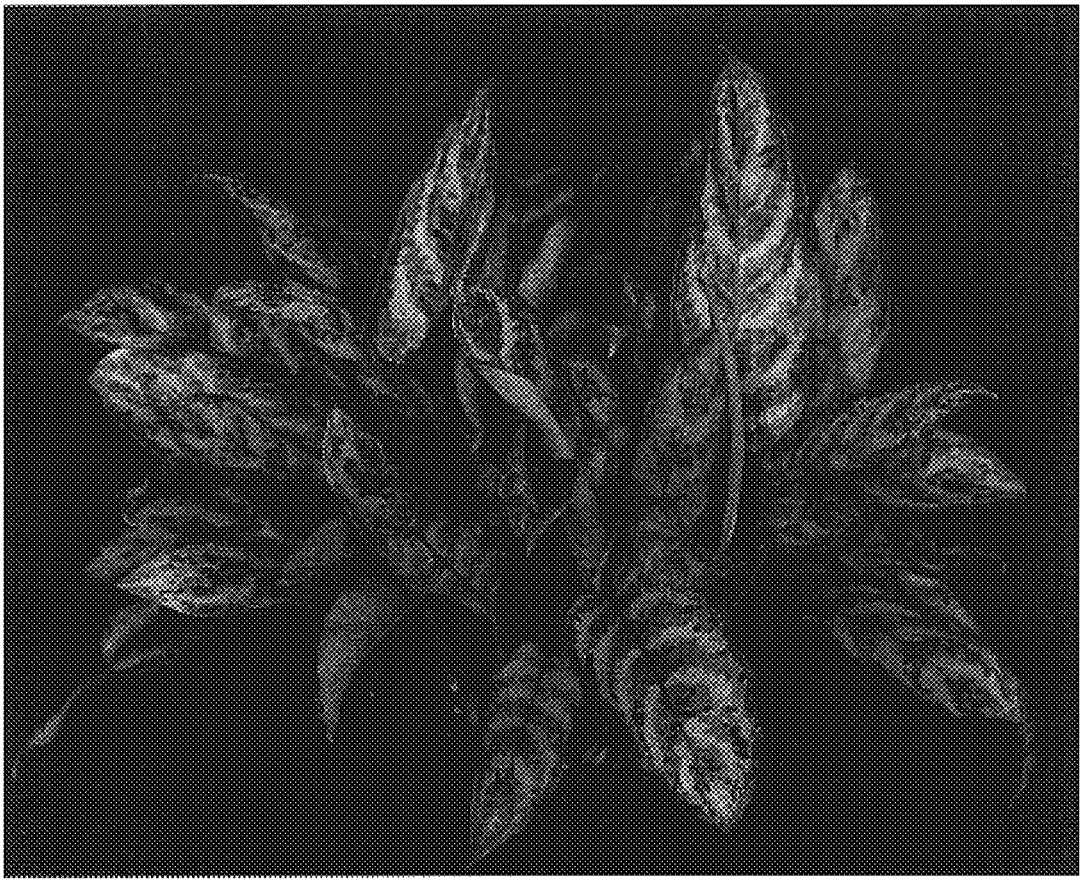

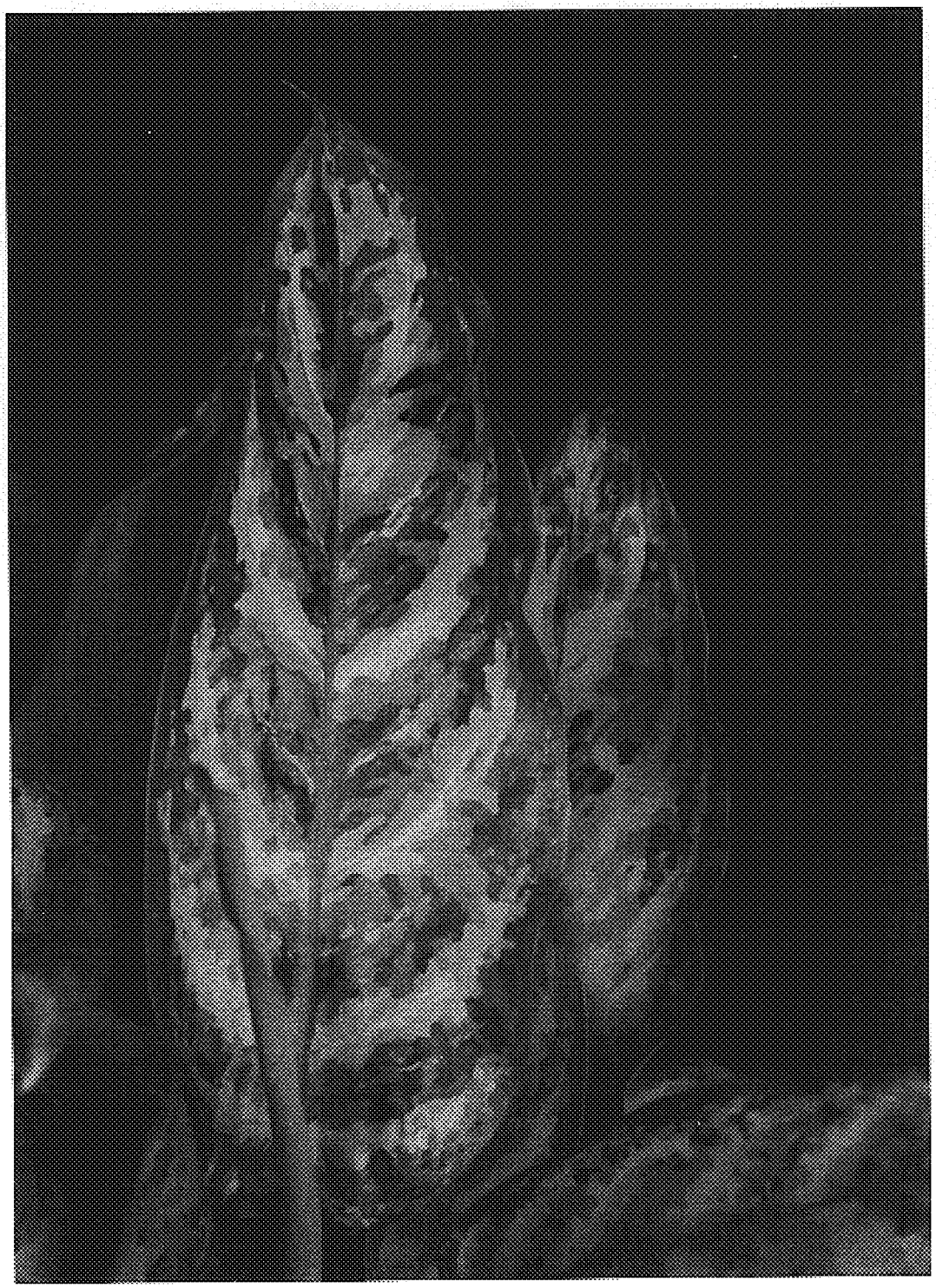

* * * * *